United States Patent [19]

Igaue et al.

[11] Patent Number: 4,904,251
[45] Date of Patent: Feb. 27, 1990

[54] DISPOSABLE DIAPER

[75] Inventors: Takamitsu Igaue, Kawanoe; Hideaki Kitaoka, Funabashi; Hiroyuki Tanji, Kawanoe, all of Japan

[73] Assignee: Uni-Charm Corporation, Ehime, Japan

[21] Appl. No.: 176,324

[22] Filed: Mar. 31, 1988

Related U.S. Application Data

[63] Continuation-in-part of Ser. No. 31,673, Mar. 30, 1987, abandoned.

[51] Int. Cl.⁴ .............................................. A41B 13/02
[52] U.S. Cl. .................................................. 604/385.2
[58] Field of Search ................... 604/385.1, 385.2, 358, 604/378, 396

[56] References Cited

FOREIGN PATENT DOCUMENTS 2161059 of 0000 United Kingdom.
2168253 of 0000 United Kingdom.
2181336 of 0000 United Kingdom.

Primary Examiner—John D. Yasko
Attorney, Agent, or Firm—Fred Philpitt

[57] ABSTRACT

A disposable diaper includes a semi-rigid absorbent body and high flexible side flaps disposed on laterally opposite side thereof. Each of said side flaps includes a first flap disposed outside said absorbent body and a second flap diverged from said first side flap. Each of said second flaps has the associated one of an elastic band incorporated therein and turned up under an elastic effect of said associated elastic band at least along a line of the divergence.

10 Claims, 8 Drawing Sheets

DISPOSABLE DIAPER

CROSS-REFERENCE TO RELATED APPLICATION

The present application is a continuation-in-part of U.S. application Ser. No. 031,673, filed Mar. 30, 1987, now abandoned.

BACKGROUND OF THE INVENTION

The present invention relates to a disposable diaper adapted to absorb and retain human excretions and more particularly to such disposable diaper to be worn by babies, sick persons, aged people and persons suffering from incontinence, in which a selected portion of each flexible side flap incorporated with elastic band is turned upwards under the elastic effect of said elastic band.

Some of the absorptive articles such as disposable diapers have already adopted the side flaps constructed to be raised so that fitting of said side flaps around the thighs of the wearer is improved and thereby leakage of excretions which would otherwise occur across the thighs can be effectively avoided, for example, as disclosed in U.S. Pat. No. 4,579,556. In accordance with the technique as disclosed by this U.S. Patent, along the outer edges of the rectangular absorbent body (layer) interposed between or sandwiched by the topsheet and the backsheet, the side flaps rise under elastic effect of the elastic bands which are incorporated into the respective side flaps along the outer edges thereof. Such rising or turning up of the side flaps is believed to occur due to a fact that a rigidity of the absorbent body is higher than that of the side flaps and, as a consequence, the elastic effect of the elastic bands transmitted to said side flaps is blocked by the outer edge of said absorbent body and converted into an effect serving to turn said side flaps up.

According to this concept, however, the absorbent body is restricted to a configuration having the substantially linear outer edges, i.e., the rectangular form in general and its width is also restricted, so that it is difficult for the absorbent body to be configured in any other shape suitable to improve fitting of the diaper around the wearer's body, for example, in the form of a sandglass. In addition, although the side flaps are certainly turned up as has been described above, such rising or turning up is merely bending of the side flaps along the outer edges of the absorbent body. Accordingly, said side flaps might be subjected to a stress-strain due to the rigidity of said absorbent body and thereby their free flexibility might tend to be hindered, unless the height (width) of said flaps is dimensioned to be relatively large and distances between the elastic gathers formed by the associated elastic bands mounted on the free ends of the respective side flaps and the associated outer edges of said absorbent body are also dimensioned to be relatively large. At the same time, said absorbent body tends to be subjected to a stress-strain due to the elastic effect of said elastic bands and thereby to be irregularly deformed, resulting in various inconveniences such as deteriorated appearance of the diaper as being worn, an uncomfortability for the wearer and poor fitting of the diaper on the wearer's body, particularly a poor sealing effect around the thighs.

A typical technique to overcome the problems encountered when the side flaps including the elastic gathers formed by the elastic bands are associated with combining with a semi-rigid absorbent body is disclosed in the U.S. Pat. No. 3,860,003. The technique disclosed in this U.S. Patent teaches that, when the side flaps are incorporated with the elastic bands along the outer sides thereof sufficiently spaced from the associated outer edges of the absorbent body, an effective seal is obtained around the thighs without significantly hindered contractibility and flexibility of the side flaps by said elastic bands due to the rigidity of said absorbent body.

However, when the elastic bands are to be disposed along the outer sides of the side flaps sufficiently spaced from the associated outer edges of the absorbent body, it will be necessary that the width of the absorbent body is dimensioned to be relatively narrow at least in the crotch area. This will result in that a capacity or a volume to absorb and retain excretions is reduced in the most important area for this purpose and thereby leakage of excretions occurs across around the thighs. Although the U.S. Pat. No. 3,860,003 intends to eliminate the drawback of the prior art that the front portion of the diaper is encouraged to blossom or pouch outwards as though it were trying to form a damp apron, this intention will not be achieved when the respective elastic bands are sufficiently spaced from the associated outer edges of the absorbent body.

Thus, the prior art anticipates no measure to overcome the above-mentioned problems which are effectively solved, according to the present invention, by a particular arrangement of the side flaps as will be described in detail later.

A principal object of the present invention is, for the purpose of effectively overcoming the inconveniences as set forth above, to provide a disposable diaper so improved to achieve an effective seal around the thighs as can not be expected from the prior art and thereby to minimize a possible leakage of excretions across around the thighs.

Other objects and advantages of the present invention will be apparent from reading the following description.

SUMMARY OF THE INVENTION

The present invention broadly resides in a disposable diaper including a water-permeable topsheet, a water-impermeable backsheet, an absorbent body interposed between said both sheets and having a semi-rigidity, water-impermeable side flaps disposed on laterally opposite sides of said absorbent body and having a high flexibility, elastic bands adapted to form elastic gathers extending longitudinally of said side flaps and tape fasteners disposed on laterally opposite sides in a rear side area of the diaper, wherein each of said side flaps includes a first flap disposed outside said absorbent body and a second flap diverged from said first side flap, having the associated one of said elastic bands incorporated therein and turned up under an elastic effect of said associated elastic band at least along a line of the divergence.

With such arrangement of the present invention, said second flap is turned up from said line of divergence transversely of said first flap so that the gather portion of said second flap functions to achieve a desired effect independently of the rigidity of said absorbent body even if the distance from the outer edge of said absorbent body to said elastic band is relatively small.

PREFERRED EMBODIMENTS OF THE INVENTION

Figure 1:
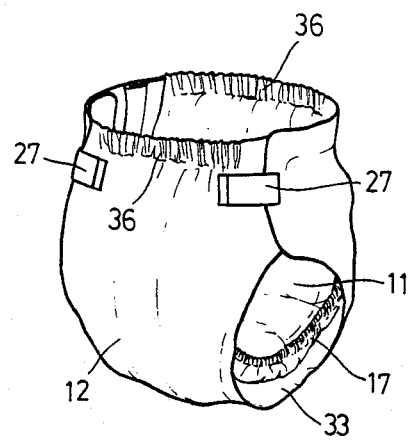
FIG. 1 is a perspective view showing a diaper constructed in accordance with the present invention as completely assembled.

Referring to FIGS. 1 through 6, a diaper of the invention comprises a water-permeable topsheet 11, a water-impermeable backsheet 12, a semi-rigid absorbent body 13 and side flaps 14. Each of said side flaps 14 consists of a first flap 16 and a second flap 17. The first flap 16 consists, in turn, of respective portions of the topsheet 11 and the backsheet 12 as well as a portion of the second flap 17 which extend outwards from each side edge of the absorbent body 13. The width of said extending portions of the topsheet 11 may be smaller than that of the backsheet 12. The second flap 17 lies upon the top surface of the first flap 16 and outside portions of these both flaps lying one upon another are so joined to each other as to define a pocket 18 therebetween. An inside portion of the second flap 17 which is not joined to the first flap 16 is turned or folded upwardly and a portion 17a thus turned or folded up is then securely joined to itself at a front side area 19 and a rear side area 20 of the diaper. A folded portion of the second flap 17 located in a crotch area defined between said front side area 19 and said rear side area 20 is provided along its free end with elastic band 22 fixed thereon under its longitudinally stretched condition with adhesive (not shown) of hot melt type and enclosed by an envelope-like edge 23 of the second flap 17. The first flap 16 is formed along its outer edge with a cut-away portion 24.

Figure 2:
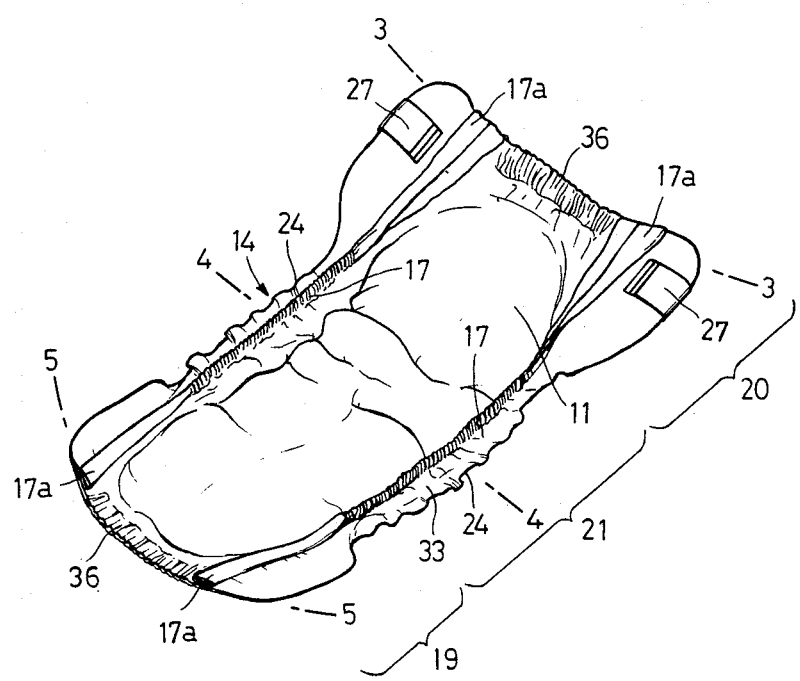
FIG. 2 is a developed perspective view showing a top side of said diaper.
Figure 3:
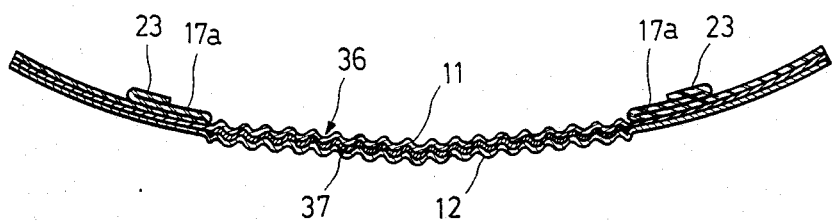
FIG. 3 is a sectional view taken along a line 3—3 in FIG. 2.
Figure 6:
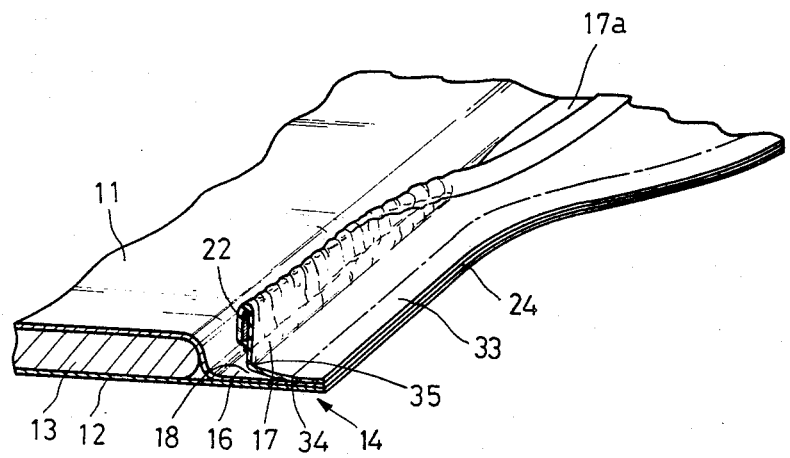
FIG. 6 is a partial perspective view showing a side portion of said diaper.
Figure 7:
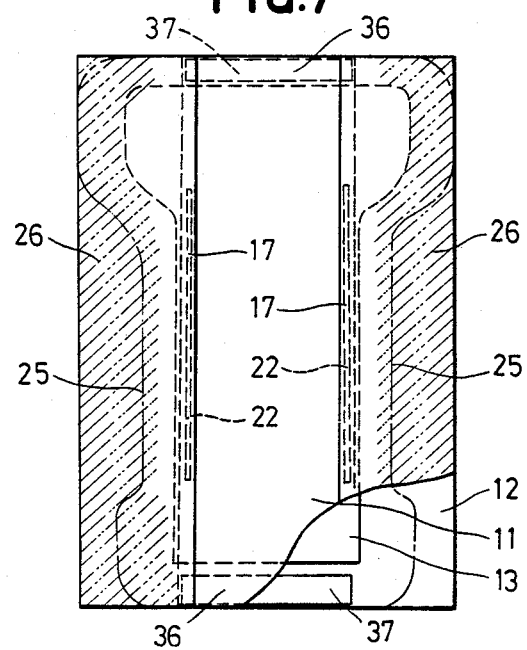
FIG. 7 is a plan view showing said diaper as in a process of its formation.
Figure 8:
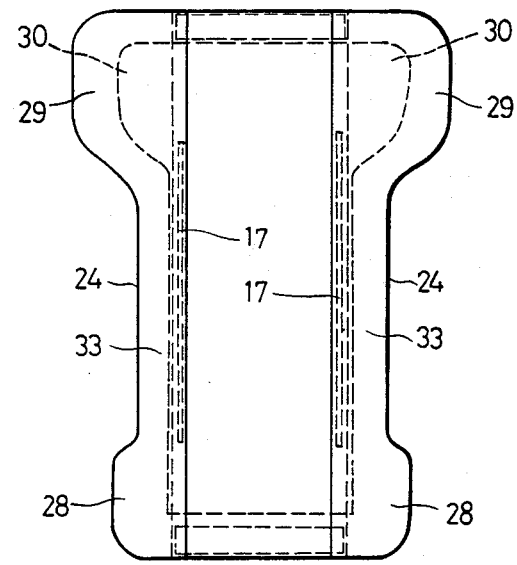
FIG. 8 is a plan view showing said diaper as having been completed after said process of formation.
Figure 9:
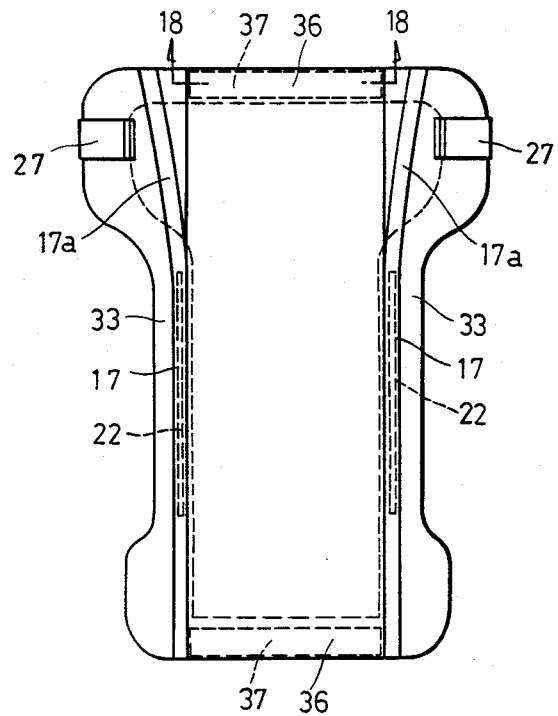
FIG. 9 is a developed plan view showing said diaper as having been longitudinally extended.

Such diaper is obtained, as seen in FIGS. 7 through 9, by sandwiching the absorbent body 13 between the rectangular topsheet 11 and the rectangular backsheet 12, disposing a pair of narrow rectangular flap sheets 17 which have previously been provided with elastic bands 22 along laterally opposite sides of the topsheet 11 (see FIG. 6), joining these to said topsheet 11 with adhesive of hot melt type or any other suitable welding means (not shown) over areas indicated by two-dotted chain lines (oblique lines), then partially cutting away the sheets 11, 12, and 17, folding the inside portion of the sheet 17 back and finally fixedly joining the portion 17a thus folded back to itself in the front side area and the rear side area thereof also by use of adhesive of hot melt type or any other suitable welding means (not shown). As seen in FIGS. 2 and 9, a transverse distance between the pair of said folded portions 17a is larger in the rear side area 20 than in the front side area 19 of the diaper. Thus, the rear side area 20 corresponding to hip of the wearer and primarily exposed to excretions is wider than the front side area 19.

In the rear side area 20, the respective side flaps 14 is provided with tape fasteners 27 carrying thereon pressure sensitive adhesive and, upon actually wearing, the diaper is assembled, as seen in FIG. 1, by securing free ends of the respective fasteners onto the front side of the diaper.

The topsheet 11 may be of fibrous nonwoven fabric, porous plastic film etc., and the backsheet 12 may be of plastic film, laminate sheet consisting of said plastic film and fibrous nonwoven fabric etc. When said laminate sheet is employed, this is used with said nonwoven fabric facing outwards. Although said plastic film is preferably air-permeable and water proof, the air-permeability will be unnecessary if there is provided means to assist ventilation through the diaper between inside and outside thereof. The absorbent body 13 may be, for example, of mat-like body consisting of fluff pulp mixed or not mixed with high-absorptivity polymer particles, covered at least on upper and lower sides with water-permeable sheets such as tissue paper and hydrophobic nets. In view of such material and configuration, it will be obviously understood that the absorbent body 13 is semi-rigid. The absorbent body 13 is securely joined to both the topsheet 11 and the backsheet 12 in a relatively stationary manner as with adhesive of hot melt type (not shown). The elastic bands 22 may be thread- or tape-like rubber, tape-like plastic foam or plastic film exhibiting an elasticity when heat-treated. These materials used to manufacture the diaper are those commonly used for the disposable diaper and those skilled in the art will easily make a choice as desired.

The first flap 16 is, as has previously been mentioned, formed by the respective portions of the topsheet 11 and the backsheet 12 extending outwards from each of the laterally opposite edges of the absorbent body 13 and a portion of the second flap 17. The second flap 17 is made of an air-permeable and water-proof sheet, preferably of fibrous nonwoven fabric which has been subjected to water-proofing with silicone resin.

In an embodiment as shown by FIGS. 8 and 9, lugs 28 laterally projecting from the front side area at opposite sides have their dimensions different from lugs 29 similarly projecting from the rear side area of the diaper, and the absorbent body 13 has lugs 30 only in the rear side area. However, the present invention is not limited to such configuration.

Figure 10:
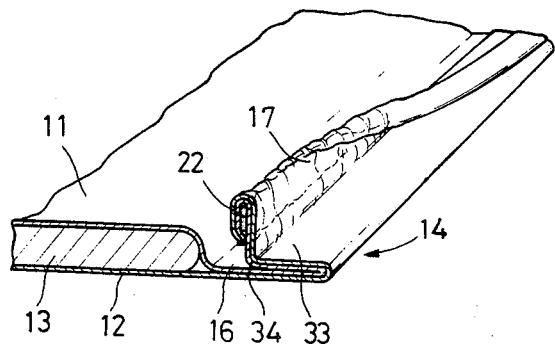
FIG. 10 through 17 are partial perspective views showing other embodiments of said side portion.
Figure 11:
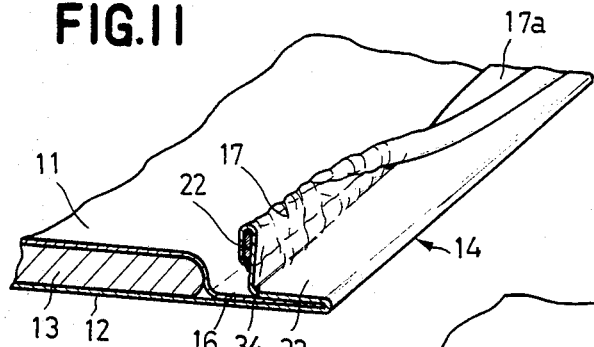

The side flaps 14 may be formed, as in an embodiment shown in FIGS. 10 and 11, by folding back the outside portion(s) of both the wide topsheet 11 and the wide backsheet 12 of only the backsheet 12. However, when said second flap 17 is different in nature from both the topsheet 11 and the backsheet 12 is used to form the side flaps 14, various advantages are obtained, which cannot be expected when the side flaps 14 are formed by the extensions of the topsheet 11 and the backsheet 12. For example, when the backsheet 12 is of air-permeable and water-proof material, the side flaps 14 may be formed by highly air-permeable and water-proof material to further reduce a stuffiness possibly occurring inside the diaper. Furthermore, even if such highly air-permeable and water-proof material is of a relatively high cost, this leads to no economical disadvantage, because the side flaps 14, particularly the second flaps 17 may be narrow relative to the backsheet 12.

Figure 12:
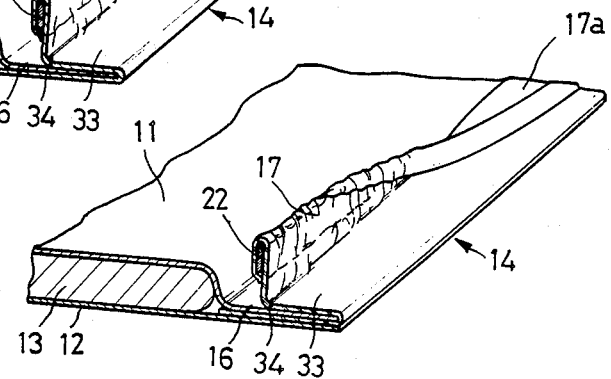

In an embodiment as shown by FIG. 12, each of the second flaps 17 is formed by sandwiching its longitudinal one side between the respective portions of the topsheet 11 and the backsheet 12 which together form the associated first flap 16, folding back this onto said portion of the topsheet 11 and joined thereonto, then turning or folding a remaining or non-joined side outwards, joining the portion 17a thus turned or folded outwards onto itself along longitudinal opposite ends of this portion, and finally providing the non-joined folded portion with the associated elastic band 22.

Figure 13:
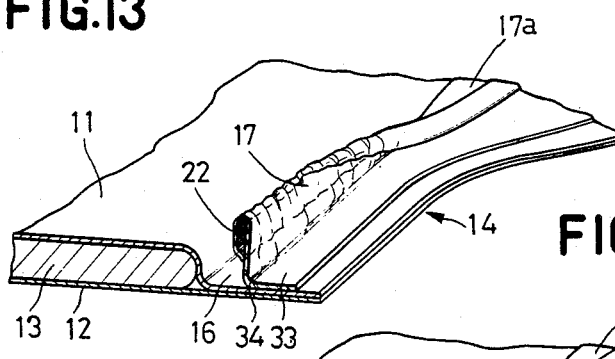

Each of the second flaps 17 in an embodiment as shown by FIG. 13 is formed by joining its longitudinal one side onto the upper side of the associated first flap 16 at a position inside the side edge of the associated first flap 16, turning or folding a remaining or non-joined side outwards, joining the portion 17a thus turned or folded outwards onto itself along longitudinal opposite ends of this portion, and finally providing a free end of the non-joined folded portion with the associated elastic band 22.

Figure 14:
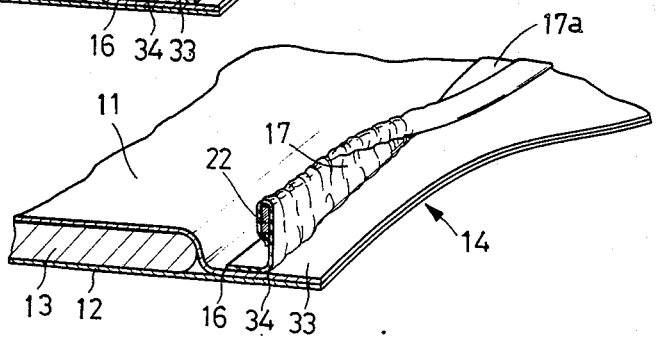

In an embodiment as shown by FIG. 14, each of the second flaps 17 is formed by laying it on the upper side of the associated first flap 16, joining it thereonto, turning or folding a remaining or non-joined portion outwards, joining the portion thus turned or folded outwards onto itself along longitudinal opposite ends of this portion and finally providing a non-joined central portion with the associated elastic band 22.

Figure 15:
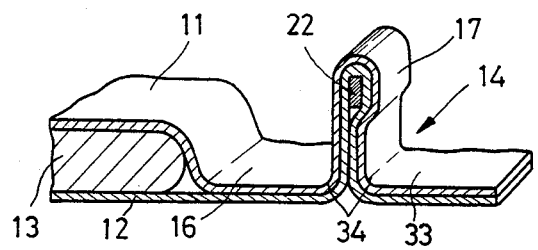

In an embodiment of FIG. 15, the second flap 17 is formed by bending the respective extensions of the topsheet 11 and the backsheet 12 upwardly in an inverted u-shape, inserting the associated elastic band 22 into a spaced defined inside a top of this bent portion and joining the inner surface of this portion together.

Figure 16:
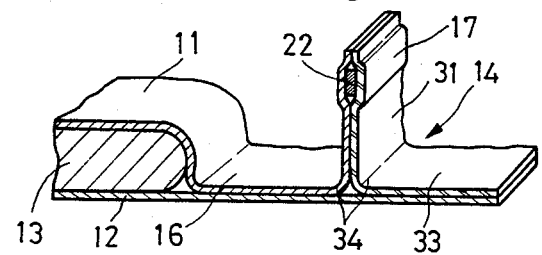

The second flap 17 in an embodiment as shown in FIG. 16 is formed by bending the extensions of the topsheet 11 upwards, joining one side of a sheet 31 onto the upper side of the backsheet 12 along an outer side portion of the extension thereof, joining the other side of said sheet 31 onto said bent portion of the topsheet 11 in symmetrical relationship therewith and inserting the associated elastic band 22 into a space defined between the top ends of these bent portions.

Figure 17:
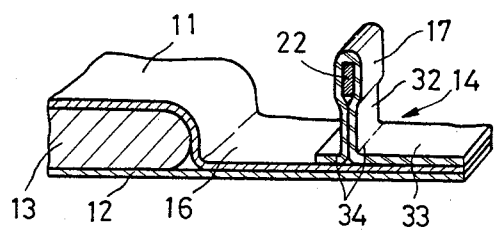

In an embodiment as shown by FIG. 17, the second flap 17 is formed joining lower ends of a sheet 32 bend in an inverted u-shape onto the extension of the topsheet 11 and inserting the associated elastic band 22 into a space defined inside a top of this bent portion.

The second flap 17 in the embodiment of FIGS. 15 through 18 is preferably laid outwards and fixedly joined along longitudinal opposite ends thereof for the reason as will be mentioned. However, the present invention is not limited to such arrangement. In all the embodiments as shown, a portion 33 extending outwards from the second flap 17 in the crotch area has no contribution to provide seals around the thighs and therefore may be omitted except when this is necessary to form the pockets 18.

The diaper constructed in the manner as has been mentioned hereinabove in accordance with the present invention provides advantages as will be set forth below.

When the pockets 18 are formed, excretions flowing towards the side flaps 14 are retained by these pockets and effectively prevented from leaking across around the thighs.

Figure 4:
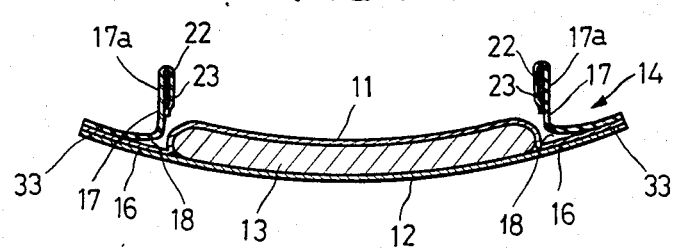
FIG. 4 is a sectional view taken along a line 4—4 in FIG. 2.
Figure 5:
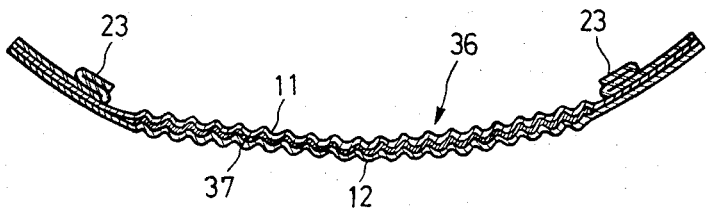
FIG. 5 is a sectional view taken along a line 5—5 in FIG. 2.

The respective elastic bands 22 give the associated second flaps 17 effective elasticity and create the gathers. Contracting force of the elastic bands 22 act substantially upon overall of the associated second flaps 17, but such contracting force is reduced or suppressed on the lines 34 along which the respective second flaps 17 diverge from the associated first flaps 16, resulting in that a portion (major portion) of said contracting force is converted into an effect serving to turn the associated second flaps 17 up from the associated first flaps 16 along said lines 34 of divergence and thus the second flaps 17 are turned or folded up independently of the outer edges of the absorbent body 13. In the case in which the folding lines 35 of the respective folded portions 17a are distinctly formed independently of said lines 34 of divergence as seen in FIGS. 4 and 6, the contracting force of the respective elastic bands 22 is reduced or suppressd also along these folding lines 35. As a consequence, even when the distance between each elastic band 22 and the associated outer edge of the absorbent body 13 is relatively small, the problems that the second flaps 17 under the contracting force of the associated elastic bands 22 might have their contractibility and flexibility affected by the rigidity of the absorbent body 13 as well as the problems that the first flaps 16 and the absorbent body 13 might be subjected to a unnatural stress-strain due to the contracting force of the respective elastic bands 22 are effectively solved. Accordingly, indecent appearance of the diaper as worn and uncomfortability for the wearer are avoided and sufficient fitting of the diaper around the wearer's body, particularly an effective seal around the thighs are achieved, minimizing leakage of excretions.

The second flaps 17 have their free ends along which the elastic bands 22 are disposed directed outwardly and their longitudinal opposite ends being fixed against the elastic effect of the elastic bands 22 tending to lay down the second flaps 17 inwardly, the second flaps 17 are normally biased under a tension enough to maintain the second flaps 17 folded upwards and thereby prevented from being folded or turned inwardly when the diaper is worn. Moreover, movement of the wearer's thighs causes the second flaps 17 to be inclined or pivoted on said fixed longitudinal opposite ends and said lines 34 of divergence so as to keep resilient contact with the wearer's skin without formation of a gap causing leakage of excretions across around the thighs.

In view of the construction and the function as mentioned above, said lines 34 of divergence can be considered as rigidity gap lines or discontinuous rigidity lines which prevent the contracting force of the respective elastic band 22 from being transmitted beyond the second flap 17 to the first flap 16. To improve the contracting force of the elastic bands 22 and the contractibility of the second flaps 17, the height of each second flap 17 should be at least 10 mm, preferably 15 to 50 mm. Distance between the outer edge of the absorbent body 13 and said line 34 of divergence is not critical, but preferably less than 50 mm. The second flaps 17 may be close to the outer edges of the absorbent body 13 so far as the second flaps 17 have a desired height and said rigidity gap lines or discontinuous rigidity lines are formed.

Figure 18:
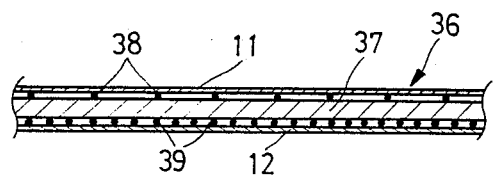
FIG. 18 is an enlarged schematic sectional view taken along a line 18—18 in FIG. 9.

Although not critical to achieve the objects of the present invention, waist flaps 36 are formed by the respective portions of the topsheet 11 and the backsheet 12 extending outwards from the longitudinal opposite ends of the absorbent body 13, as seen in FIGS. 2, 3, 5 and 7 through 9, and 18. Second elastic bands 37 are disposed under longitudinal tension in a sandwich manner between the waist flaps 36, i.e., between the topsheet 11 and the backsheet 12. These elastic bands 37 are of plastic foam, particularly of polyurethane foam preferably having a thickness of 1 to 3 mm, a width of at least 5 mm and open cells of 20 to 70 kg/m$^3$. The elastic bands 37 are joined, as shown in FIG. 18, onto the topsheet 11 and the backsheet 12 with, for example, with adhesive 38, 39 of hot melt type. Adhesive 38, 39 linearly extends transversely of the elastic bands 37 and applied onto the bands at regular intervals longitudinally of the bands or transversely of the diaper. Application interval of adhesive 38 used to join the topsheet 11 and the elastic bands 37 is larger than that for adhesive 39 used to join the backsheet 12 and the elastic bands 37. Thereby, the contractibility on an area on which the topsheet 11 is joined to the elastic bands 37 is stronger than the contractibility on an area on which the backsheet 12 is joined to the elastic bands 37. In consequence, the waist flaps 36 appropriately follow curves of the wearer's body to achieve a good fit. Said manner in which adhesive is applied so as to establish a difference of said contractibility may be so modified that said adhesive is applied in a stripe extending longitudinally of the elastic bands 37 as a stripe extending longitudinally of said bands 37 while applied over a relatively wide area between the backsheet 12 and the elastic bands 37. In other words, the particular manner of application is not critical so long as said difference in the contractibility can be established. Furthermore, the elastic bands 37 preferably have their outer edges exposed between the respective outer edges of the topsheet 11 and the backsheet 12 so that a ventilation of the diaper between the inside and outside thereof is facilitated through the elastic bands 37 made of plastic foam having open cells. To this end, it is required for this plastic foam to have said thickness and said cell density. Moreover, a distance between the longitudinal outer edge of the absorbent body 13 and the inner edge of the associated elastic band 37 is preferably at least 5 mm. With such distance, the fitness of the waist flaps 36 to the wearer's body, particularly the belly is further improved.

Figure 19:
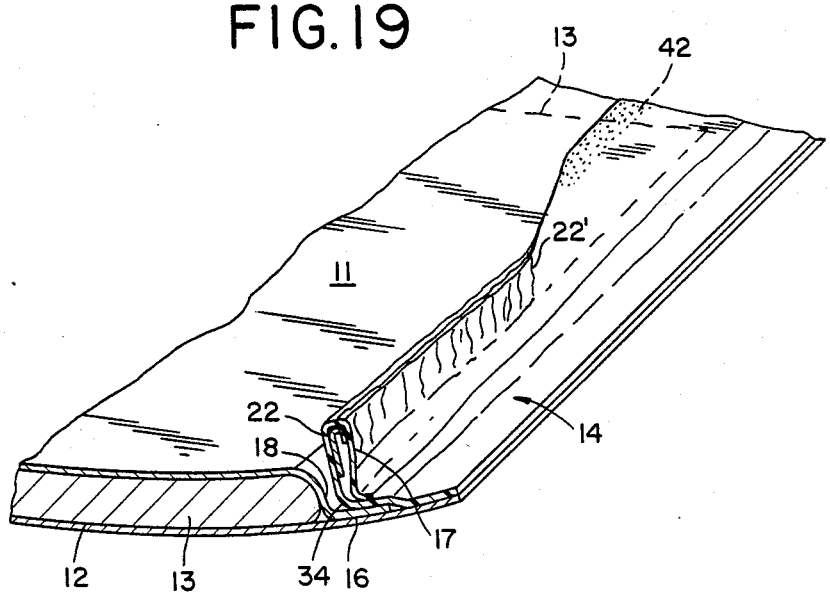
FIG. 19 is a partial perspective view of another embodiment of said side portion.
Figure 20:
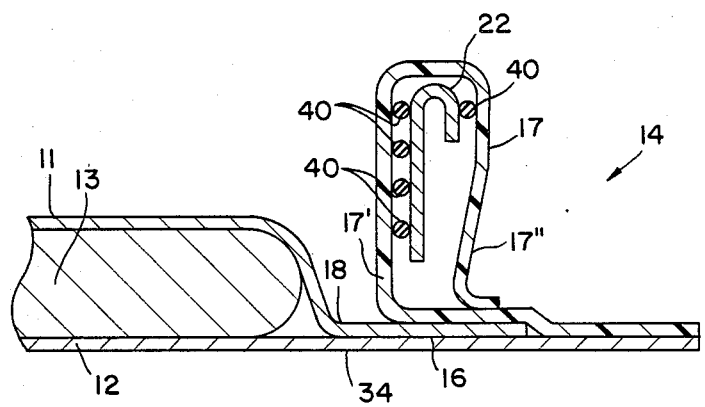
FIG. 20 is a relatively enlarged cross-sectional view of the embodiment of said side portion shown in FIG. 19.

FIGS. 19 and 20 show a further embodiment of the side flaps 14 of the present disposable diaper. As in the previous embodiment, a pair of generally upstanding leg gathers are provided in the form of second flaps 17 which diverge upwardly from first flaps 16. A pair of the longitudinally extending leg gathers are provided on respective lateral sides of the absorbent body 13 interposed between liquid-permeable topsheet 11 and liquid-impermeable backsheet 12.

Each leg gather includes the flap 17, and the inner elastic element 22, with the flap 17 thus forming an outer covering sleeve for the inner elastic element. As illustrated in FIGS. 19 and 20, the outer covering sleeve includes a portion secured to at least one of topsheet 11 and backsheet 12, and in the particular embodiment illustrated, such portion overlies and is secured to lateral marginal portions of both the topsheet 11 and the backsheet 12.

Notably, each elastic element 22 is folded or doubled upon itself within its respective covering sleeve along at least a portion of the length of each element 22, and preferably along substantially the entire length of the elastic elements. Thus, each elastic element defines an outer surface and an inner surface thereof. As shown in FIG. 20, the leg gather further includes a plurality of adhesive lines 40 or like securement means which secure the elastic element within its respective covering sleeve. As illustrated in FIG. 20, the adhesive lines 40 are provided along the outer surface of the elastic element 22.

Adhesive lines 40 may extend along the entire length of the elastic element 22, or may be provided only at selected portions of the element 22. For example, the adhesive lines may be discontinuous and intermittent in nature, and can be provided at regularly spaced intervals. Further, such adhesive lines or like securement means can be provided only at the longitudinal end portions of the elastic elements 22, with the central portion of each element 22 being substantially unsecured within its respective covering sleeve. In such an arrangement, there can be a tendency for the unsecured central portions of the elastic elements to unfold from the folded construction.

This form of the leg gather, with each inner elastic element 22 being folded along at least a portion of its longitudinal extent, provides several distinct advantages for the present diaper. The elastic element 22 is preferably formed from plastic foam, particularly polyurethane foam, generally of the type for forming elastic waistbands 37. This type of foam is preferred for its inherent cushioning effect, thus enhancing comfort of the diaper for the wearer. As will be appreciated, this cushioning effect is enhanced by providing a double thickness of the foam elastic 22 at each leg gather for contact with the legs of the wearer.

Additionally, the natural resiliency of the elastic material can result in some tendency of the folded portions of the elastic elements 22 to unfold and exert outward force components on the respective covering sleeve. This can further enhance the desirable cushioning effect which is provided. Further, the non-woven fabric of each covering sleeve is gathered under the influence of the elastic element therein, with the soft texture of this gathered material further contributing to the desired cushioning effect for the comfort of the wearer.

This folded configuration for the elastic element 22 promotes its positioning within the outer covering sleeve provided by flap 17 such that the covering sleeve is in close conformance to the elastic element. Specifically, it is desirable that the non-woven fabric of the outer covering sleeve be positioned closely to the uppermost portion of the elastic element, in the illustrated embodiment whereat the elastic element is folded onto itself. Since it can be difficult to achieve such close conformance by separately folding the outer covering sleeve about the elastic element 22 (whether the element 22 is a single thickness, or folded), the illustrated arrangement permits the elastic element to be joined to the non-woven fabric of the outer covering sleeve with both in a substantially unfolded condition, secured together by adhesive lines 40 or the like, and thereafter folded in unison to provide the illustrated configuration. In accordance with this further embodiment, both the inner and outer portions 17', 17'', of the covering sleeve provided by flap 17 are turned outwardly relative to absorbent body 13, toward the lateral marginal edge of the diaper (FIG. 20). The inner portion 17' thus extends outwardly generally beneath the elastic element 22 when the leg gather is generally vertically upstanding relative to the absorbent body, with the outer portion of the covering sleeve secured to this outwardly turned inner portion.

Further features of this illustrated embodiment should be noted in FIG. 19. As previously discussed, the outer covering sleeve provided by flap 17 has its longitudinal ends extending beyond the longitudinal ends of the inner elastic element 22, with the longitudinal end of the elastic element 22 indicated at 22' in FIG. 19. In the previously described embodiments, the longitudinal ends of the flap 17 are folded outwardly and downwardly and secured in this generally flattened manner (see FIG. 6).

In distinction, the longitudinal end of the flap 17 shown in FIG. 19 is folded generally inwardly and downwardly, and secured in this generally flattened configuration such as by adhesive 42 between the lower side of the flap 17 and the topsheet 11. Further, the longitudinal ends of the outer covering sleeve provided by flap 17 may be arranged to extend beyond the respective longitudinal end of the absorbent body 13, again as illustrated in FIG. 19.

The illustrated inward securement of the longitudinal ends of the flaps 17 can be provided at both longitudinal ends of the flap, or may be provided in combination with the outward securement arrangement such as shown in FIG. 6. Specifically, the forward longitudinal ends of the flaps 17 may be secured inwardly (such as illustrated in FIG. 19), while the rearward longitudinal ends of the flaps 17 may be secured outwardly, such as generally illustrated in FIG. 6. This arrangement can desirably provide a tailored fit for the diaper, in that the leg gathers tend to generally converge toward each other from the back to the front of the diaper. This configuration has been found to provide more space in the rearward, seat portion of the diaper to better accommodate the buttocks of the wearer, while conforming and tailoring the forward portion of the diaper to the forward lower torso of the wearer.

Numerous other modifications and variations can be effected without departing from the true spirit and scope of the novel concept of the present invention. It is to be understood that no limitation with respect to the specific embodiments is intended or should be inferred. The disclosure is intended to cover by the appended claims all such modifications as fall within the scope of the claims.

What is claimed is:

1. A disposable diaper, comprising:
   a liquid-permeable topsheet (11), a liquid-impermeable backsheet (12), and an absorbent body (13) interposed between said topsheet (11) and said backsheet (12),
   said diaper including a pair of generally upstanding elastic leg gathers extending longitudinally of said diaper on respective lateral sides of said absorbent body, each said leg gather including an inner elastic element (22), and an outer covering sleeve including a portion secured to at least one of said topsheet (11) and said backsheet (12),
   each said elastic element (22) being in the form of an elongated elastic strip and being folded over within the respective covering sleeve (17) along at least a portion of its length to thereby establish an outer folded surface and an inner folded surface of said elastic element and to thereby increase the effective thickness of at least said portion of said elastic element, each said leg gather further including securement means (40) securing said elastic element (22) within the respective covering sleeve (17), said securement means (40) being provided along at least a portion of the longitudinal extent of the outer surface of the elastic element (22).

2. A disposable diaper in accordance with claim 1 wherein
   each said elastic element is folded within the respective covering sleeve along substantially the entire length of the elastic element.

3. A disposable diaper in accordance with claim 1 wherein
   inner and outer portions of the covering sleeve of each said leg gather are arranged to extend generally outwardly away from said absorbent body.

4. A disposable diaper in accordance with claim 1 wherein
   the longitudinal ends of said outer covering sleeve of each said leg gather extend beyond the respective longitudinal ends of the elastic element positioned within the covering sleeve.

5. A disposable diaper, comprising:
   a liquid-permeable topsheet, a liquid-impermeable backsheet, and an absorbent body interposed between said topsheet and said backsheet,
   said diaper including a pair of generally upstanding leg gathers extending longitudinally of said diaper on respective lateral sides of said absorbent body (13), each said leg gather including an inner elastic element (22) and an outer covering sleeve (17) comprising a component separate from said liquid-impermeable topsheet (11) and said liquid-impermeable backsheet (12) and including a base portion secured to at least one of said topsheet (11) and said backsheet (12),
   the longitudinal ends of the covering sleeve (17) of each said leg gather extending beyond the longitudinal ends of the respective inner elastic element (22) therein, with said longitudinal ends of said covering sleeve (17) secured downwardly to at least one of said topsheet (11) and said backsheet (12),
   said outer covering sleeve (17) of each said leg gather having a free edge intermediate said longitudinal ends thereof, said respective inner elastic element (22) being positioned within said covering sleeve (17) at said free edge thereof, each said covering sleeve (17) further including inner (17') and outer (17") portions each extending from said free edge in substantially parallel relationship to each other to said base portion of said outer covering sleeve (17), said inner portion (17') being positioned outwardly relative to said absorbent body toward the marginal edge of the diaper, with said inner portion (17') of said covering sleeve (17) extending outwardly generally beneath the respective one of said inner elastic elements (22) and beneath said outer sleeve portion (17") when the leg gather is generally vertically upstanding relative to the absorbent body (13) so that said outward extension of said inner portion (17') provides said base portion of said outer covering sleeve (17).

6. A disposable diaper in accordance with claim 5, wherein
one of said longitudinal ends of each said covering sleeve is secured generally inwardly, and the other longitudinal end of the covering sleeve is secured generally outwardly.

7. A disposable diaper in accordance with claim 5 wherein
said elastic element of each said leg gather is folded along at least a portion of its length within the respective covering sleeve.

8. A disposable diaper, comprising:
a liquid-permeable topsheet, a liquid-impermeable backsheet, and an absorbent body interposed between said topsheet and said backsheet,
said diaper including a pair of generally upstanding elastic leg gathers extending longitudinally of said diaper on respective lateral sides of said absorbent body, each said leg gather including an inner elastic element in the form of an elongated elastic strip and an outer covering sleeve including a portion secured to at least one of said topsheet and said backsheet,
each said elastic element within the respective covering sleeve having what amounts to a folded over portion that extends along at least a portion of the length of the elastic element so as to thereby establish an outer folded surface and an inner folded surface of said elastic element, said inner folded surface of each said elastic element being free of adhesive means so that each said folded elastic element is free to exert an outward force component on its respective covering sleeve to enhance the cushioning effect of each upstanding elastic leg gather.

9. A disposable diaper in accordance with claim 8 including
securement means securing at least a portion of the outer folded surface of each elastic element with the interior of its respective covering sleeve.

10. A disposable diaper comprising a water-permeable topsheet (11), a water impermeable backsheet (12), a semi-rigid absorbent body (13) interposed between said topsheet and backsheet, water impermeable flexible side flaps extending laterally outwardly from opposite sides of said absorbent body, at least one elastic element (22) extending longitudinally of each of said side flaps and fasteners disposed on opposite sides of one end of said diaper, characterized in that each of said side flaps comprises a first side flap (16) and a second side flap (17), said first side flap (16) extending laterally outwardly from said absorbent body (13) and said second side flap (17) extending from said first side flap (16) in a laterally divergent manner and in that said elastic elements (22) are associated with each of said second side flaps (17) and act thereon to cause at least an edge portion thereof to be held over at least a central portion of the length thereof in a substantially upstanding position relative to the first side flap (16) from which it extends, said second flap (17) having its longitudinal one side joined onto the upper side of said first flap (16) and the other side folded back outwards of which longitudinally opposite ends are fixed onto the front side area and the rear side area of the diaper and thereby defines a pocket (18) between said first flap (16) and an unfolded-back other side of said second flap (17) and prevents said second flap (17) being turned inwardly when the diaper is worn.

* * * * *